(12) United States Patent
Bathe et al.

(10) Patent No.: US 7,226,763 B2
(45) Date of Patent: Jun. 5, 2007

(54) PROCESS FOR PREPARING L-AMINO ACIDS WITH CORYNEBACTERIA WITH ENHANCED NUCLEOTIDE SEQUENCES CODING FOR PKND

(75) Inventors: Brigitte Bathe, Salzkotten (DE); Indra Schroeder, Steinhagen (DE); Mike Farwick, Bielefeld (DE); Thomas Hermann, Bielefeld (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 11/110,837

(22) Filed: Apr. 21, 2005

(65) Prior Publication Data

US 2005/0255566 A1    Nov. 17, 2005

Related U.S. Application Data (62) Division of application No. 09/949,971, filed on Sep. 12, 2001, now Pat. No. 6,927,052.

(60) Provisional application No. 60/297,266, filed on Jun. 12, 2001.

(30) Foreign Application Priority Data

Sep. 12, 2000  (DE)  ............................... 100 44 948
Apr. 25, 2001  (DE)  ............................... 101 20 094

(51) Int. Cl.
*C12P 13/04*   (2006.01)
*C12N 9/10*    (2006.01)
*C12N 1/20*    (2006.01)
*C12N 15/00*   (2006.01)
*C07H 21/04*   (2006.01)

(52) U.S. Cl. ...................... 435/106; 435/115; 435/183; 435/193; 435/252.3; 435/252.32; 435/320.1; 536/23.2

(58) Field of Classification Search .............. 435/106, 435/115, 183, 193, 252.3, 252.32, 320.1, 435/252.33; 536/23.2
See application file for complete search history.

(56) References Cited

U.S. PATENT DOCUMENTS 4,411,997 A    10/1983   Shimazaki et al.

FOREIGN PATENT DOCUMENTS

EP    1 108 790    6/2001

WO    WO 00/17379    3/2000

OTHER PUBLICATIONS

Oster et al. Gene Expr Patterns. Apr. 2006;6(4):400-8. Epub Dec. 27, 2005.*
Eiglmeier, et al., Accession L78813. Jun. 15, 1996 (Alignment No. 1).
Barash, et al., Accession AAV522202. Oct. 23, 1998 (Alignment No. 2).
S.T. Cole, et al., Database EMBL 'Online!' AN AL021957, XP-002191212, pp. 1-3, "Mycobacterium Tuberculosis H37Rv Complete Genome; Segment 97/162", Feb. 23, 1998.
Y.Av-Gay, et al., Trends in Microbiology, vol. 8, No. 5, pp. 238-244, XP-002191211, "The Eukaryotic-Like SER/THR Protein Kinases of Mycobacterium Tuberculosis" May 2000.
B. Schrumpf, et al., Journal of Bacteriology, vol. 173, No. 14, pp. 4510-4516, XP-000884180, "A Functionally Split Pathway for Lysine Synthesis in *Corynebacterium Glutamicum*" Jul. 1991.
S. Nakagawa, et al. Database EMBL 'Online!, AN AX127150, XP-002191244, "Sequence 7066 From Patent EP1108790", May 10, 2001.
S. Nakagawa, et al., Database AMBL 'Online!', AN AX125968, XP-002191701, p. 1, "Sequence 5884 From Patent EP1108790", May 10, 2001.
Attwood, et al., Which craft is best in bioinformatics? Comput. Chem. 2001, vol. 25(4), pp. 329-339.
Ponting, C.P. Issues in predicting protein function from seuqence. Brief. Bioinform. Mar. 2001, vol. 2(1), pp. 19-29.
Roest-Crollius, et al. Accession AL232074. May 15, 2000.

* cited by examiner

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

An isolated polynucleotide which contains a polynucleotide sequence selected from the group comprising:
(a) a polynucleotide which is at least 70% identical to a polynucleotide coding for a polypeptide containing the amino acid sequence of SEQ ID No. 2,
(b) a polynucleotide coding for a polypeptide containing an amino acid sequence which is at least 70% identical to the amino acid sequence of SEQ ID No. 2,
(c) a polynucleotide which is complementary to the polynucleotides of (a) or (b), and
(d) a polynucleotide containing at least 15 consecutive nucleotides of the polynucleotide sequence of (a), (b), or (c),
and a fermentation process for the preparation of L-amino acids using corynebacteria in which at least the pknD gene is amplified, and to the use, as hybridization probes, of polynucleotides containing the sequences according to the invention.

12 Claims, 1 Drawing Sheet

Figure 1: Map of the plasmid pk18mobsacB pknD XL

PROCESS FOR PREPARING L-AMINO ACIDS WITH CORYNEBACTERIA WITH ENHANCED NUCLEOTIDE SEQUENCES CODING FOR PKND

CROSS-REFERENCE TO RELATED APPLICATIONS

This application is a divisional application of U.S. application Ser. No. 09/949,971 filed Sep. 12, 2001, now U.S. Pat. No. 6,927,052, which claims benefit to U.S. Provisional Application Ser. No. 60/297,266, filed Jun. 12, 2001 and identified herein by reference.

BACKGROUND OF THE INVENTION

1. Field of the Invention

The present invention provides nucleotide sequences from corynebacteria coding for the pknD gene and a fermentation process for the preparation of amino acids using bacteria in which the endogenous pknD gene is amplified.

2. Description of the Background

L-Amino acids, especially L-lysine, are used in human medicine, in the pharmaceutical industry, in the food industry, and, in particular, in animal nutrition. It is known that amino acids are prepared by the fermentation of strains of corynebacteria, especially *Corynebacterium glutamicum*. Because of their great importance, attempts are constantly being made to improve such preparative processes. Improvements to these processes may relate to measures involving the fermentation technology, e.g. stirring and oxygen supply, or the composition of the nutrient media, e.g. the sugar concentration during fermentation, or the work-up to the product form, e.g. by ion exchange chromatography, or the intrinsic productivity characteristics of the microorganism itself.

The productivity characteristics of these microorganisms are improved by using methods of mutagenesis, selection and mutant choice to give strains which are resistant to antimetabolites or auxotrophic for metabolites important in regulation, and produce amino acids.

Methods of recombinant DNA technology have also been used for some years to improve L-amino acid-producing strains of *Corynebacterium* by amplifying individual amino acid biosynthesis genes and studying the effect on amino acid production. However, there remains a need for improved methods of producing L-amino acids.

SUMMARY OF THE INVENTION

It is an object of the present invention to provide novel measures for improving the preparation of amino acids by fermentation.

It is another object of the present invention to provide nucleic acid sequences which are useful for the production of amino acids.

Accordingly, the present invention provides an isolated polynucleotide from corynebacteria which contains a polynucleotide sequence coding for the pknD gene and is selected from the following group:

(a) a polynucleotide which is at least 70% identical to a polynucleotide coding for a polypeptide containing the amino acid sequence of SEQ ID No. 2, (b) a polynucleotide coding for a polypeptide containing an amino acid sequence which is at least 70% identical to the amino acid sequence of SEQ ID No. 2, (c) a polynucleotide which is complementary to the polynucleotides of (a) or (b), and (d) a polynucleotide containing at least 15 consecutive nucleotides of the polynucleotide sequence of (a), (b) or (c), where the polypeptide preferably has the activity of protein kinase D.

The present invention also provides the above-mentioned polynucleotide, which is preferably a replicable DNA containing:

(i) the nucleotide sequence shown in SEQ ID No. 1, or (ii) at least one sequence corresponding to sequence (i) within the degeneracy of the genetic code, or (iii) at least one sequence which hybridizes with the sequence complementary to sequence (i) or (ii), and optionally (iv) neutral sense mutations in (i).

The present invention additionally provides:

a replicable polynucleotide, especially DNA, containing the nucleotide sequence as shown in SEQ ID No. 1, a polynucleotide coding for a polypeptide containing the amino acid sequence as shown in SEQ ID No. 2, a vector containing the polynucleotide according to the invention, especially a shuttle vector or plasmid vector, and corynebacteria which contain the vector or in which the endogenous pknD gene is amplified.

The present invention additionally provides a fermentation process for the preparation of an L-amino acid, comprising:

(a) fermenting in a medium corynebacteria producing the L-amino acid, wherein at least the endogenous pknD gene or nucleotide sequences coding therefor are amplified in the corynebacteria, (b) enriching the L-amino acid in the medium or in the cells of the corynebacteria, and (c) isolating the L-amino acid.

The present invention also provides polynucleotides consisting substantially of a polynucleotide sequence which are obtainable by screening, by means of hybridization, of an appropriate gene library of a Corynebacterium, containing the complete gene or parts thereof, with a probe containing the sequence of the polynucleotide of the invention according to SEQ ID No. 1 or a fragment thereof, and by isolation of the polynucleotide sequence.

BRIEF DESCRIPTION OF THE FIGURE

A more complete appreciation of the invention and many of the attendant advantages thereof will be readily obtained as the same becomes better understood by reference to the following Figures in conjunction with the detailed description below.

The abbreviations and designations used have the following meaning. The length data are to be understood as approximate values.

sacB: sacB gene
oriV: Replication origin V
KmR: Kanamycin resistance
XbaI: Cleavage site of the restriction enzyme XbaI
pknD': Incomplete fragment of the pknD gene from DM1547

DETAILED DESCRIPTION OF THE INVENTION

When L-amino acids or amino acids are mentioned hereafter, this is understood to refer to one or more amino acids, including their salts, selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

When L-lysine or lysine is mentioned hereafter, this is understood to refer to not only the bases but also the salts, e.g. lysine monohydrochloride or lysine sulfate.

As hybridization probes for RNA, cDNA and DNA, polynucleotides containing the sequences according to the invention are suitable for isolating the full length of nucleic acids, or polynucleotides or genes, coding for protein kinase D, or for isolating nucleic acids, or polynucleotides or genes, whose sequence exhibits a high degree of similarity to the sequence of the pknD gene. They are also suitable for incorporation into so-called arrays, micro-arrays or DNA chips for detecting and determining the corresponding polynucleotides. Polynucleotides containing the sequences according to the invention are further suitable as primers for the preparation, by the polymerase chain reaction (PCR), of DNA of genes coding for protein kinase D.

Such oligonucleotides serving as probes or primers contain at least 25, 26, 27, 28, 29 or 30, preferably at least 20, 21, 22, 23 or 24 and very particularly preferably at least 15, 16, 17, 18 or 19 consecutive nucleotides. Oligonucleotides with a length of at least 31, 32, 33, 34, 35, 36, 37, 38, 39 or 40 or at least 41, 42, 43, 44, 45, 46, 47, 48, 49 or 50 nucleotides are also suitable. Oligonucleotides with a length of at least 100, 150, 200, 250 or 300 nucleotides may also be suitable.

As used herein, the term "isolated" refers to a material, e.g., a nucleic acid, separated from its natural environment.

"Polynucleotide" refers in general to polyribonucleotides and polydeoxyribonucleotides, it being possible for the RNAs or DNAs in question to be unmodified or modified.

The polynucleotides according to the invention include a polynucleotide according to SEQ ID No. 1 or a fragment prepared therefrom, as well as polynucleotides which are in particular at least 70% to 80%, preferably at least 81% to 85%, particularly preferably at least 86% to 90% and very particularly preferably at least 91%, 93%, 95%, 97% or 99% identical to the polynucleotide according to SEQ ID No. 1 or a fragment prepared therefrom. "Polypeptides" are understood as meaning peptides or proteins containing two or more amino acids bonded via peptide links.

The polypeptides according to the invention include a polypeptide according to SEQ ID No. 2, especially those with the biological activity of protein kinase D and also those which are at least 70% to 80%, preferably at least 81% to 85%, particularly preferably at least 86% to 90% and very particularly preferably at least 91%, 93%, 95%, 97% or 99% identical to the polypeptide according to SEQ ID No. 2, and have the activity of protein kinase D.

The invention further relates to a fermentation process for the preparation of amino acids selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, using corynebacteria which, in particular, already produce amino acids and in which the nucleotide sequences coding for the pknD gene are amplified and, in particular, overexpressed.

In this context the term "amplification" describes the increase in the intracellular activity, in a microorganism, of one or more enzymes which are coded for by the appropriate DNA, for example by increasing the copy number of the gene(s) or allele(s), using a strong promoter or using a gene or allele coding for an appropriate enzyme with a high activity, and optionally combining these measures.

By amplification measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The microorganisms provided by the present invention can produce L-amino acids from glucose, sucrose, lactose, fructose, maltose, molasses, starch or cellulose or from glycerol and ethanol. The microorganisms can be representatives of corynebacteria, especially of the genus *Corynebacterium*. The species *Corynebacterium glutamicum* may be mentioned in particular in the genus *Corynebacterium*, which is known to those skilled in the art for its ability to produce L-amino acids.

The following known wild-type strains:
*Corynebacterium glutamicum* ATCC13032
*Corynebacterium acetoglutamicum* ATCC 15806
*Corynebacterium acetoacidophilum* ATCC 13870
*Corynebacterium thermoaminogenes* FERM BP-1539
*Corynebacterium melassecola* ATCC 17965
*Brevibacterium flavum* ATCC14067
*Brevibacterium lactofermentum* ATCC13869, and
*Brevibacterium divaricatum* ATCC14020 and L-amino acid-producing mutants or strains prepared therefrom, are particularly suitable strains of the genus *Corynebacterium*, especially of the species *Corynebacterium glutamicum* (*C. glutamicum*).

The novel pknD gene of *C. glutamicum* coding for the enzyme protein kinase D (EC 2.7.1.37) has been isolated using the procedures described herein.

The first step in isolating the pknD gene or other genes of *C. glutamicum* is to construct a gene library of this microorganism in *Escherichia coli* (*E. coli*). The construction of gene libraries is documented in generally well-known textbooks and manuals. Examples which may be mentioned are the textbook by Winnacker entitled From Genes to Clones, Introduction to Gene Technology (Verlag Chemie, Weinheim, Germany, 1990) or the manual by Sambrook et al. entitled Molecular Cloning, A Laboratory Manual (Cold Spring Harbor Laboratory Press, 1989). A very well-known gene library is that of the *E. coli* K-12 strain W3110, which was constructed by Kohara et al. (Cell 50, 495–508 (1987)) in λ vectors. Bathe et al. (Molecular and General Genetics 252, 255–265, 1996) describe a gene library of *C. glutamicum* ATCC13032, which was constructed using cosmid vector SuperCos I (Wahl et al., 1987, Proceedings of the National Academy of Sciences USA 84, 2160–2164) in the *E. coli* K-12 strain NM554 (Raleigh et al., 1988, Nucleic Acids Research 16, 1563–1575). Börmann et al. (Molecular Microbiology 6(3), 317–326 (1992)) in turn describe a gene library of *C. glutamicum* ATCC13032 using cosmid pHC79 (Hohn and Collins, Gene 11, 291–298 (1980)).

A gene library of *C. glutamicum* in *E. coli* can also be constructed using plasmids like pBR322 (Bolivar, Life Sciences 25, 807–818 (1979)) or pUC9 (Vieira et al., 1982, Gene 19, 259–268). Restriction- and recombination-defective *E. coli* strains are particularly suitable as hosts, an example being the strain DH5αmcr, which has been described by Grant et al. (Proceedings of the National Academy of Sciences USA 87 (1990) 4645–4649). The long DNA fragments cloned with the aid of cosmids can then in turn be subcloned into common vectors suitable for sequencing, and subsequently sequenced, e.g. as described by Sanger et al. (Proceedings of the National Academy of Sciences of the United States of America 74, 5463–5467, 1977).

The DNA sequences obtained can then be examined with known algorithms or sequence analysis programs, e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The novel DNA sequence of *C. glutamicum* coding for the pknD gene was found and, as SEQ ID No. 1, forms part of the present invention. Furthermore, the amino acid sequence of the corresponding protein was derived from the DNA sequence by the methods described above. The resulting amino acid sequence of the pknD gene product is shown in SEQ ID No. 2.

Coding DNA sequences which result from SEQ ID No. 1 due to the degeneracy of the genetic code are also within the scope of the present invention. Likewise, DNA sequences which hybridize with SEQ ID No. 1 or portions of SEQ ID No. 1 are also within the scope of the present invention. Furthermore, conservative amino acid exchanges, e.g. the exchange of glycine for alanine or of aspartic acid for glutamic acid in proteins, are known to those skilled in the art as "sense mutations", which do not cause a fundamental change in the activity of the protein, i.e. they are neutral. It is also known that changes at the N- and/or C-terminus of a protein do not substantially impair its function or may even stabilize it. Those skilled in the art can find information on this subject in Ben-Bassat et al. (Journal of Bacteriology 169, 751–757 (1987)), O'Regan et al. (Gene 77, 237–251 (1989)), Sahin-Toth et al. (Protein Sciences 3, 240–247 (1994)) and Hochuli et al. (Bio/Technology 6, 1321–1325 (1988)), inter alia, and in well-known textbooks on genetics and molecular biology. Amino acid sequences which correspondingly result from SEQ ID No. 2 are also within the scope of the present invention.

Likewise, DNA sequences which hybridize with SEQ ID No. 1 or portions of SEQ ID No. 1 are also within the scope of the present invention. Finally, DNA sequences which are prepared by the polymerase chain reaction (PCR) using primers resulting from SEQ ID No. 1 are additonally within the scope of the present invention. Such oligonucleotides typically have a length of at least 15 nucleotides.

Those skilled in the art can find instructions on the identification of DNA sequences by means of hybridization in inter alia the manual entitled "The DIG System User's Guide for Filter Hybridization" from Boehringer Mannheim GmbH (Mannheim, Germany, 1993) and in Liebl et al. (International Journal of Systematic Bacteriology (1991) 41, 255–260), inter alia. Hybridization takes place under stringent conditions; in other words, only hybrids for which the probe and the target sequence, i.e. the polynucleotides treated with the probe, are at least 70% identical are formed. It is known that the stringency of hybridization, including the washing steps, is influenced or determined by varying the buffer composition, the temperature and the salt concentration. The hybridization reaction is preferably carried out under relatively low stringency compared with the washing steps (Hybaid Hybridisation Guide, Hybaid Limited, Teddington, UK, 1996).

The hybridization reaction can be carried out for example using a 5×SSC buffer at a temperature of approx. 50° C.–68° C., it also being possible for probes to hybridize with polynucleotides which are less than 70% identical to the sequence of the probe. Such hybrids are less stable and are removed by washing under stringent conditions. This can be achieved for example by lowering the salt concentration to 2×SSC and subsequently to 0.5×SSC if necessary (The DIG System User's Guide for Filter Hybridization, Boehringer Mannheim, Mannheim, Germany, 1995), the temperature being adjusted to approx. 50° C.–68° C. It is possible to lower the salt concentration to 0.1×SSC if necessary. By raising the hybridization temperature in approx. 1–2° C. steps from 50° C. to 68° C., it is possible to isolate polynucleotide fragments which are e.g. at least 70%, at least 80% or at least 90% to 95% identical to the sequence of the probe used. Further instructions on hybridization are commercially available in the form of kits (e.g. DIG Easy Hyb from Roche Diagnostics GmbH, Mannheim, Germany, Catalog No. 1603558).

Those skilled in the art can find instructions on the amplification of DNA sequences with the aid of the polymerase chain reaction (PCR) in the manual by Gait entitled Oligonucleotide Synthesis: A Practical Approach (IRL Press, Oxford, UK, 1984) and in Newton and Graham: PCR (Spektrum Akademischer Verlag, Heidelberg, Germany, 1994), inter alia.

It has been found that, after overexpression of the pknD gene, the production of amino acids by corynebacteria is improved.

Overexpression can be achieved by increasing the copy number of the appropriate genes or mutating the promoter and regulatory region or the ribosome binding site located upstream from the structural gene. Expression cassettes incorporated upstream from the structural gene work in the same way. Inducible promoters additionally make it possible to increase the expression in the course of the production of amino acid by fermentation. Measures for prolonging the life of the mRNA also improve the expression. Furthermore, the enzyme activity is also enhanced by preventing the degradation of the enzyme protein. The genes or gene constructs can either be located in plasmids of variable copy number or integrated and amplified in the chromosome. Alternatively, it is also possible to achieve overexpression of the genes in question by changing the composition of the media and the culture technique.

Those skilled in the art can find relevant instructions in Martin et al. (Bio/Technology 5, 137–146 (1987)), Guerrero et al. (Gene 138, 35–41 (1994)), Tsuchiya and Morinaga (Bio/Technology 6, 428–430 (1988)), Eikmanns et al. (Gene 102, 93–98 (1991)), EP 0 472 869, U.S. Pat. No. 4,601,893, Schwarzer and Pühler (Bio/Technology 9, 84–87 (1991)), Reinscheid et al. (Applied and Environmental Microbiology 60, 126–132 (1994)), LaBarre et al. (Journal of Bacteriology 175, 1001–1007 (1993)), WO 96/15246, Malumbres et al. (Gene 134, 15–24 (1993)), JP-A-10-229891, Jensen and Hammer (Biotechnology and Bioengineering 58, 191–195 (1998)) and Makrides (Microbiological Reviews 60, 512–538 (1996)), inter alia, and in well-known textbooks on genetics and molecular biology.

For amplification, the pknD gene according to the invention has been overexpressed for example with the aid of episomal plasmids. Suitable plasmids are those which are replicated in corynebacteria. Numerous known plasmid vectors, e.g. pZ1 (Menkel et al., Applied and Environmental Microbiology (1989) 64, 549–554), pEKEx1 (Eikmanns et al., Gene 102, 93–98 (1991)) or pHS2-1 (Sonnen et al., Gene 107, 69–74 (1991)), are based on cryptic plasmids pHM1519, pBL1 or pGA1. Other plasmid vectors, e.g. those based on pCG4 (U.S. Pat. No. 4,489,160), pNG2 (Serwold- Davis et al., FEMS Microbiology Letters 66, 119–124 (1990)) or pAG1 (U.S. Pat. No. 5,158,891), can be used in the same way.

Other suitable plasmid vectors are those which make it possible to use the gene amplification process by integration into the chromosome, as described for example by Reinscheid et al. (Applied and Environmental Microbiology 60, 126–132 (1994)) for the duplication or amplification of the hom-thrB operon. In this method the complete gene is cloned into a plasmid vector which can replicate in a host (typically *E. coli*), but not in *C. glutamicum*. Examples of suitable vectors are pSUP301 (Simon et al., Bio/Technology 1, 784–791 (1983)), pK18mob or pK19mob (Schäfer et al., Gene 145, 69–73 (1994)), pGEM-T (Promega Corporation, Madison, Wis., USA), pCR2.1-TOPO (Shuman (1994), Journal of Biological Chemistry 269, 32678–84; U.S. Pat. No. 5,487,993), pCR®Blunt (Invitrogen, Groningen, The Netherlands; Bernard et al., Journal of Molecular Biology 234, 534–541 (1993)), pEM1 (Schrumpf et al., 1991, Journal of Bacteriology 173, 4510–4516) or pBGS8 (Spratt et al., 1986, Gene 41, 337–342). The plasmid vector containing the gene to be amplified is then transferred to the desired strain of *C. glutamicum* by conjugation or transformation. The method of conjugation is described for example in Schäfer et al. (Applied and Environmental Microbiology 60, 756–759 (1994)). Methods of transformation are described for example in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a crossover event, the resulting strain contains at least two copies of the gene in question.

It has also been found that amino acid exchanges in the section between position 661 and position 669 of the amino acid sequence of protein kinase D, shown in SEQ ID No. 2, improve the production of amino acids, especially lysine, by corynebacteria. Preferably, L-glutamic acid in position 664 is exchanged for any other proteogenic amino acid except L-glutamic acid, and/or glycine in position 666 is exchanged for any other proteogenic amino acid except glycine.

The exchange in position 664 is preferably for L-lysine or L-arginine, especially L-lysine, and the exchange in position 666 is preferably for L-serine or L-threonine, especially L-serine.

SEQ ID No. 3 shows the base sequence of the pknD-1547 allele contained in the strain DM1547. The pknD-1547 allele codes for a protein whose amino acid sequence is shown in SEQ ID No. 4. The protein contains L-lysine in position 664 and L-serine in position 666. The DNA sequence of the pknD-1547 allele (SEQ ID No. 3) contains the base adenine in place of the base guanine contained in the pknD wild-type gene (SEQ ID No. 1) in position 2501, and the base adenine in place of the base guanine in position 2507. Mutagenesis can be carried out by conventional methods using mutagenic substances such as N-methyl-N'-nitro-N-nitrosoguanidine or ultraviolet light. Mutagenesis can also be carried out using in vitro methods such as treatment with hydroxylamine (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or mutagenic oligonucleotides (T. A. Brown: Gentechnologie für Einsteiger (Gene Technology for Beginners), Spektrum Akademischer Verlag, Heidelberg, 1993), or the polymerase chain reaction (PCR) as described in the manual by Newton and Graham (PCR, Spektrum Akademischer Verlag, Heidelberg, 1994).

The corresponding alleles or mutations are sequenced and introduced into the chromosome by the method of gene replacement, for example as described in Peters-Wendisch et al. (Microbiology 144, 915–927 (1998)) for the pyc gene of *C. glutamicum*, in Schäfer et al. (Gene 145, 69–73 (1994)) for the hom-thrB gene region of *C. glutamicum* or in Schäfer et al. (Journal of Bacteriology 176, 7309–7319 (1994)) for the cg1 gene region of *C. glutamicum*. The corresponding alleles or the associated proteins can optionally be amplified in turn.

In addition it can be advantageous for the production of L-amino acids to amplify and, in particular, overexpress not only the pknD gene but also one or more enzymes of the particular biosynthetic pathway, the glycolysis, the anaplerosis, the citric acid cycle, the pentose phosphate cycle or the amino acid export, and optionally regulatory proteins.

Thus, for the production of L-amino acids, one or more endogenous genes selected from the following group can be amplified and, in particular, overexpressed in addition to amplification of the pknD gene:

the dapA gene coding for dihydrodipicolinate synthase (EP-B-0 197 335), the gap gene coding for glyceraldehyde 3-phosphate dehydrogenase (Eikmanns (1992), Journal of Bacteriology 174, 6076–6086), the tpi gene coding for triose phosphate isomerase (Eikmanns (1992), Journal of Bacteriology 174, 6076–6086), the pgk gene coding for 3-phosphoglycerate kinase (Eikmanns (1992), Journal of Bacteriology 174, 6076–6086), the zwf gene coding for glucose-6-phosphate dehydrogenase (JP-A-09224661), the pyc gene coding for pyruvate carboxylase (DE-A-198 31 609), the lysC gene coding for a feedback-resistant aspartate kinase (Accession no. P26512; EP-B-0387527; EP-A-0699759), the lysE gene coding for lysine export (DE-A-195 48 222), The hom gene coding for homoserine dehydrogenase (EP-A-0131171), the ilvA gene coding for threonine dehydratase (Möckel et al., Journal of Bacteriology (1992) 8065–8072)) or the ilvA(Fbr) allele coding for a feedback-resistant threonine dehydratase (Möckel et al., (1994), Molecular Microbiology 13, 833–842), the ilvBN gene coding for acetohydroxy acid synthase (EP-B-0356739), the ilvD gene coding for dihydroxy acid dehydratase (Sahm and Eggeling (1999), Applied and Environmental Microbiology 65, 1973–1979), the zwa1 gene coding for the Zwa1 protein (DE 199 59 328.0, DSM13115).

In addition to amplification of the pknD gene, it can also be advantageous for the production of L-amino acids to attenuate one or more genes selected from the following group:

the pck gene coding for phosphoenol pyruvate carboxykinase (DE 199 50 409.1, DSM13047), the pgi gene coding for glucose-6-phosphate isomerase (U.S. Ser. No. 09/396,478, DSM12969), the poxB gene coding for pyruvate oxidase (DE 199 51 975.7, DSM13114), the zwa2 gene coding for the Zwa2 protein (DE 199 59 327.2, DSM13113), and, in particular, to reduce the expression.

In this context the term "attenuation" describes the reduction or switching-off of the intracellular activity, in a microorganism, of one or more enzymes (proteins) which are coded for by the appropriate DNA, for example by using a weak promoter or using a gene or allele coding for an appropriate enzyme with a low activity, or inactivating the appropriate gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

It can also be advantageous for the production of amino acids not only to overexpress the pknD gene but also to switch off unwanted secondary reactions (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention are also provided by the invention and can be cultivated for the production of amino acids continuously or discontinuously by the batch process, the fed batch process or the repeated fed batch process. A summary of known cultivation methods is described in the textbook by Chmiel (Bioprozesstechnik 1. Einführung in die Bioverfahrenstechnik (Bioprocess Technology 1. Introduction to Bioengineering) (Gustav Fischer Verlag, Stuttgart, 1991)) or in the textbook by Storhas (Bioreaktoren und periphere Einrichtungen (Bioreactors and Peripheral Equipment) (Vieweg Verlag, Brunswick/Wiesbaden, 1994)).

The culture medium to be used must appropriately meet the demands of the particular strains. Descriptions of culture media for various microorganisms can be found in "Manual of Methods for General Bacteriology" of the American Society for Bacteriology (Washington D.C., USA, 1981).

Carbon sources which can be used are sugars and carbohydrates, e.g. glucose, sucrose, lactose, fructose, maltose, molasses, starch and cellulose, oils and fats, e.g. soybean oil, sunflower oil, groundnut oil and coconut fat, fatty acids, e.g. palmitic acid, stearic acid and linoleic acid, alcohols, e.g. glycerol and ethanol, and organic acids, e.g. acetic acid. These substances can be used individually or as a mixture.

Nitrogen sources which can be used are organic nitrogen-containing compounds such as peptones, yeast extract, meat extract, malt extract, corn steep liquor, soybean flour and urea, or inorganic compounds such as ammonium sulfate, ammonium chloride, ammonium phosphate, ammonium carbonate and ammonium nitrate. The nitrogen sources can be used individually or as a mixture.

Phosphorus sources which can be used are phosphoric acid, potassium dihydrogenphosphate or dipotassium hydrogenphosphate or the corresponding sodium salts. The culture medium must also contain metal salts, e.g. magnesium sulfate or iron sulfate, which are necessary for growth. Finally, essential growth-promoting substances such as amino acids and vitamins can be used in addition to the substances mentioned above. Suitable precursors can also be added to the culture medium. The feed materials can be added to the culture all at once or fed in appropriately during cultivation.

The pH of the culture is controlled by the appropriate use of basic compounds such as sodium hydroxide, potassium hydroxide, ammonia or aqueous ammonia, or acidic compounds such as phosphoric acid or sulfuric acid. Foaming can be controlled using antifoams such as fatty acid polyglycol esters. The stability of plasmids can be maintained by adding suitable selectively acting substances, e.g. antibiotics, to the medium. Aerobic conditions are maintained by introducing oxygen or oxygen-containing gaseous mixtures, e.g. air, into the culture. The temperature of the culture is normally 20° C. to 45° C. and preferably 25° C. to 40° C. The culture is continued until the formation of the desired product has reached a maximum. This objective is normally achieved within 10 hours to 160 hours. Methods of determining L-amino acids are well-known in the art. They can be analyzed for example by ion exchange chromatography with subsequent ninhydrin derivation, as described by Spackman et al. (Analytical Chemistry 30 (1958) 1190), or by reversed phase HPLC, as described by Lindroth et al. (Analytical Chemistry (1979) 51, 1167–1174).

A pure culture of the *Corynebacterium glutamicum* strain DM1547 was deposited as DSM 13994 in the Deutsche Sammlung für Mikroorganismen und Zellkulturen (German Collection of Microorganisms and Cell Cultures (DSMZ), Brunswick, Germany) on Jan. 16, 2001 under the terms of the Budapest Treaty.

A pure culture of the *Escherichia coli* strain S17-1/pK18mobsacB_pknD_XL was deposited as DSM 14410 in the Deutsche Sammlung für Mikroorganismen und Zellkulturen (German Collection of Microorganisms and Cell Cultures (DSMZ, Brunswick, Germany) on Jul. 18, 2001 under the terms of the Budapest Treaty.

The fermentation process according to the invention is used for the preparation of amino acids.

The present invention also provides a method of identifying nucleic acids which code for protein kinase B or have a high degree of similarity to the sequence of the pknB gene, comprising:

contacting a sample with the polynucleotide of claim 1 under conditions suitable for the polynucleotide to hybridize to another nucleic acid which codes for protein kinase B or have a high degree of similarity to the sequence of the pknB gene.

In one embodiment, the "another nucleic acid" mentioned above may be RNA, cDNA, or DNA. In another embodiment, the method is conducted on an array, micro-array, or DNA chip.

EXAMPLES

Having generally described this invention, a further understanding can be obtained by reference to certain specific examples which are provided herein for purposes of illustration only and are not intended to be limiting unless otherwise specified.

The isolation of plasmid DNA from *Escherichia coli* and all the techniques of restriction, Klenow treatment and alkaline phosphatase treatment were carried out according to Sambrook et al. (Molecular Cloning. A Laboratory Manual (1989), Cold Spring Harbor Laboratory Press, Cold Spring Harbor, N.Y., USA). Methods of transforming *Escherichia coli* are also described in this manual. The composition of common nutrient media, such as LB or TY medium, can also be found in the manual by Sambrook et al.

Example 1

Preparation of a Genomic Cosmid Gene Library from *Corynebacterium glutamicum* ATCC13032

Chromosomal DNA from *Corynebacterium glutamicum* ATCC13032 was isolated as described by Tauch et al. (1995, Plasmid 33, 168–179) and partially cleaved with the restriction enzyme Sau3AI (Amersham Pharmacia, Freiburg, Germany, product description Sau3AI, code no. 27-0913-02). The DNA fragments were dephosphorylated with shrimp alkaline phosphatase (Roche Diagnostics GmbH, Mannheim, Germany, product description SAP, code no. 1758250). The DNA of cosmid vector SuperCos1 (Wahl et al. (1987), Proceedings of the National Academy of Sciences USA 84, 2160–2164), obtained from Stratagene (La Jolla, USA, product description SuperCos1 Cosmid Vector Kit, code no. 251301), was cleaved with the restriction enzyme XbaI (Amersham Pharmacia, Freiburg, Germany, product description XbaI, code no. 27-0948-02) and also dephosphorylated with shrimp alkaline phosphatase.

The cosmid DNA was then cleaved with the restriction enzyme BamHI (Amersham Pharmacia, Freiburg, Germany, product description BamHI, code no. 27-0868-04). The cosmid DNA treated in this way was mixed with the treated ATCC13032 DNA and the mixture was treated with T4 DNA ligase (Amersham Pharmacia, Freiburg, Germany, product description T4 DNA ligase, code no. 27-0870-04). The ligation mixture was then packaged into phages using Gigapack II XL Packing Extract (Stratagene, La Jolla, USA, product description Gigapack II XL Packing Extract, code no. 200217).

For infection of the *E. coli* strain NM554 (Raleigh et al., 1988, Nucleic Acid Research 16, 1563–1575), the cells were taken up in 10 mM MgSO$_4$ and mixed with an aliquot of the phage suspension. Infection and titering of the cosmid library were carried out as described by Sambrook et al. (1989, Molecular Cloning: A Laboratory Manual, Cold Spring Harbor), the cells being plated on LB agar (Lennox, 1955, Virology 1, 190) containing 100 mg/l of ampicillin. After incubation overnight at 37° C., recombinant single clones were selected.

Example 2

Isolation and Sequencing of the pknD Gene

The cosmid DNA of a single colony was isolated with the Qiaprep Spin Miniprep Kit (product no. 27106, Qiagen, Hilden, Germany) in accordance with the manufacturer's instructions and partially cleaved with the restriction enzyme Sau3AI (Amersham Pharmacia, Freiburg, Germany, product description Sau3AI, product no. 27-0913-02). The DNA fragments were dephosphorylated with shrimp alkaline phosphatase (Roche Diagnostics GmbH, Mannheim, Germany, product description SAP, product no.1758250). After separation by gel electrophoresis, the cosmid fragments in the size range from 1500 to 2000 bp were isolated with the QiaExII Gel Extraction Kit (product no. 20021, Qiagen, Hilden, Germany).

The DNA of sequencing vector pZero-1, obtained from Invitrogen (Groningen, The Netherlands, product description Zero Background Cloning Kit, product no. K2500-01), was cleaved with the restriction enzyme BamHI (Amersham Pharmacia, Freiburg, Germany, product description BamHI, product no. 27-0868-04). Ligation of the cosmid fragments into sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then introduced into the *E. coli* strain DH5αMCR (Grant, 1990, Proceedings of the National Academy of Sciences USA 87, 4645–4649) by electroporation (Tauch et al. 1994, FEMS Microbiol. Letters 123, 343–7) and plated on LB agar (Lennox, 1955, Virology 1, 190) containing 50 mg/l of zeocin.

Plasmid preparation of the recombinant clones was carried out with Biorobot 9600 (product no. 900200, Qiagen, Hilden, Germany). Sequencing was carried out by the dideoxy chain termination method of Sanger et al. (1977, Proceedings of the National Academy of Sciences USA 74, 5463–5467) with modifications by Zimmermann et al. (1990, Nucleic Acids Research 18, 1067). The "RR dRhodamin Terminator Cycle Sequencing Kit" from PE Applied Biosystems (product no. 403044, Weiterstadt, Germany) was used. Separation by gel electrophoresis and analysis of the sequencing reaction were carried out in a "Rotiphorese NF acrylamide/bisacrylamide" gel (29:1) (product no. A124.1, Roth, Karlsruhe, Germany) with the "ABI Prism 377" sequencer from PE Applied Biosystems (Weiterstadt, Germany).

The raw sequence data obtained were then processed using the Staden programming package (1986, Nucleic Acids Research 14, 217–231), version 97-0. The individual sequences of the pZero-1 derivatives were assembled into a cohesive contig. Computer-assisted coding region analysis was performed with the XNIP program (Staden, 1986, Nucleic Acids Research 14, 217–231).

The nucleotide sequence obtained is shown in SEQ ID No. 1. Analysis of the nucleotide sequence gave an open reading frame of 2223 base pairs, which was called the pknD gene. The pknD gene codes for a protein of 740 amino acids.

Example 3

Preparation of a Replacement Vector for Replacement of the pknD Allels

Chromosomal DNA was isolated from the strain DSM13994 by the method of Eikmanns et al. (Microbiology 140:1817–1828 (1994)). On the basis of the sequence of the pknD gene known for *C. glutamicum* from example 2, the following oligonucleotides were chosen for the polymerase chain reaction (see also SEQ ID No. 5 and SEQ ID No. 6):

```
pknD_XL-A1:
5' (tct aga) cgg ttg gtg gtt cgg ttc ag 3' pknD_XL-E1:
5' (tct aga) agc ggc aat gcc ggt gag ta 3'
```

The primers shown were synthesized by MWG Biotech (Ebersberg, Germany) and the PCR reaction was carried out by the PCR method of Karreman (BioTechniques 24:736–742, 1998) with Pwo-Polymerase from Boehringer. The primers pknD_XL-A1 and pknD_XL-E1 each contain an inserted cleavage site for the restriction enzyme XbaI, these being indicated in parentheses in the representation. With the aid of the polymerase chain reaction, a 1.6 kb DNA section is amplified and isolated, this carrying the pknD gene or allele.

The amplified DNA fragment of approx. 1.6 kb length, which carries the pknD allele of the strain DSM13994, was cleaved with the restriction enzyme XbaI, identified by electrophoresis in a 0.8% agarose gel, isolated from the gel and purified by the conventional methods (QIAquick Gel Extraction Kit, Qiagen, Hilden).

Figure 1:
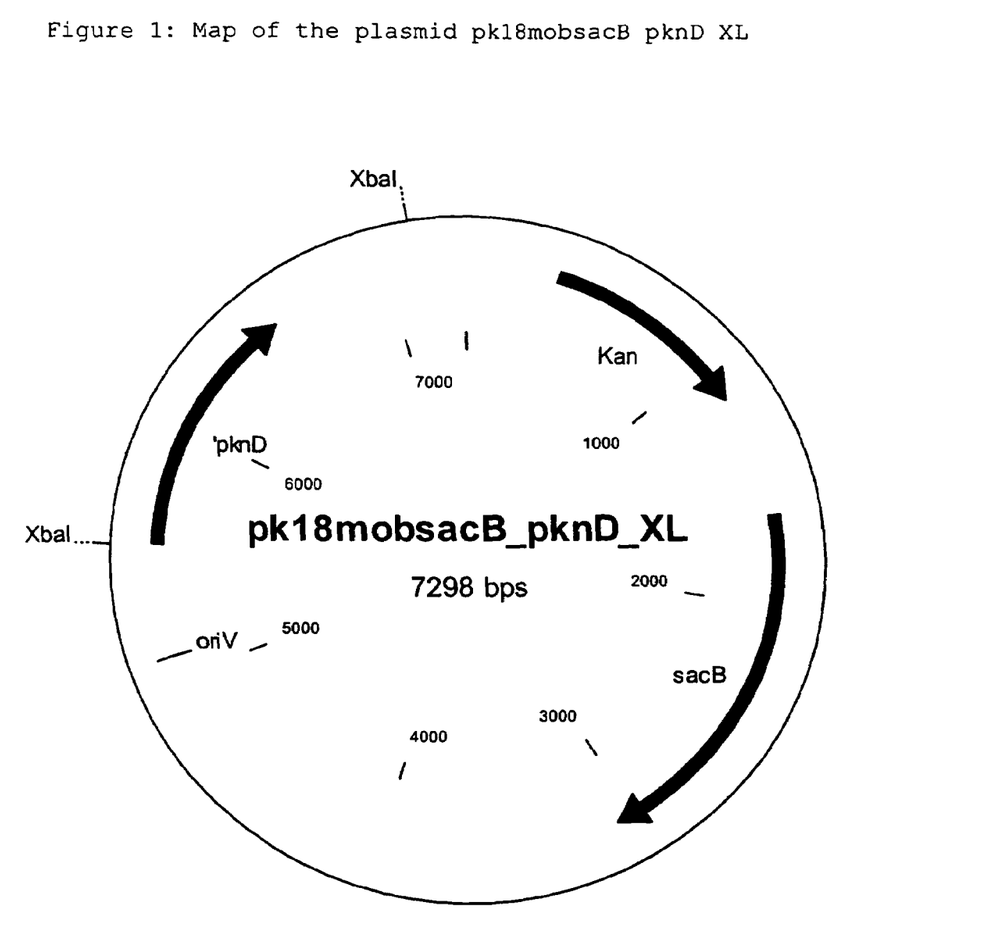
FIG. 1: Map of the plasmid pK18mobsacB_pknD_XL.

The plasmid pK18mobsacB (Jäger et al., Journal of Bacteriology, 1:784–791(1992)) was also cleaved with the restriction enzyme XbaI. The plasmid pK18mobsacB and the PCR fragment were ligated. The *E. coli* strain S17-1 (Simon et al., 1993, Bio/Technology 1:784–791) was then electroporated with the ligation batch (Hanahan, In: DNA Cloning. A Practical Approach. Vol. I, IRL-Press, Oxford, Washington D.C., USA, 1985). Selection of plasmid-carrying cells was carried out by plating out the transformation batch on LB Agar (Sambrook et al., Molecular cloning: a laboratory manual. $2^{nd}$ Ed. Cold Spring Harbor Laboratory Press, Cold Spring Harbor, N.Y., 1989), which had been supplemented with 25 mg/l kanamycin. Plasmid DNA was isolated from a transformant with the aid of the QIAprep Spin Miniprep Kit from Qiagen and checked by restriction with the restriction enzyme XbaI and subsequent agarose gel electrophoresis (0.8%). The plasmid was designated pK18mobsacB_pknD_XL and is shown in FIG. 1.

Obviously, numerous modifications and variations of the present invention are possible in light of the above teachings. It is therefore to be understood that within the scope of the appended claims, the invention may be practiced otherwise than as specifically described herein.

All of the publications cited above are incorporated herein by reference.

This application is based on German Patent Application Serial No. 100 44 948.4, filed on Sep. 12, 2000; and German Patent Application Serial No. 101 20 094.3, filed on Apr. 25, 2001, which are incorporated herein by reference.

What is claimed is:

1. A fermentation process for the preparation of an L-amino acid, comprising:
   (a) fermenting in a medium corynebacteria producing the L-amino acid, wherein a nucleotide sequence which encodes a protein kinase D (pknD) polypeptide is amplified in the corynebacteria, and
   (b) enriching the L-amino acid in the medium or in the cells of the corynebacteria wherein the nucleotide sequence is selected from the group consisting of: (a) a nucleotide sequence shown in SEQ ID NO: 1, (b) a polynucleotide which is at least 90% identical to the polynucleotide of SEQ ID NO: 1, wherein said polynucleotide codes for a polypeptide having protein kinase D activity, (c) a polynucleotide coding for a polypeptide comprising the amino acid sequence of SEQ ID NO: 2, and (d) a sequence which hybridizes with SEQ ID NO: 1, wherein hybridization comprises washing in 0.5×SSC at a temperature of 68° C., and which encodes a protein with protein kinase D activity.

2. The process of claim 1, wherein the L-amino acid is L-lysine.

3. The process of claim 1, wherein the L-amino acid is selected from the group consisting of L-asparagine, L-threonine, L-serine, L-glutamate, L-glycine, L-alanine, L-cysteine, L-valine, L-methionine, L-isoleucine, L-tyrosine, L-phenylalanine, L-histidine, L-tryptophan, and L-arginine.

4. The process of claim 1, wherein the endogenous pknD gene or the nucleotide encoding a pknD polypeptide is overexpressed.

5. The process of claim 1, wherein the polynucleotide encoding a pknD polypeptide is amplified.

6. The process of claim 1, wherein the polynucleotide encoding a pknD polypeptide is overexpressed.

7. The process of claim 1, wherein corynebacteria are Corynebacterium glutamicum.

8. The process of claim 1, which further comprises isolating the L-amino acid.

9. The process of claim 1, wherein the nucleotide sequence is a nucleotide sequence shown in SEQ ID NO: 1.

10. The process of claim 1, wherein the nucleotide sequence is a polynucleotide which is at least 90% identical to the polynucleotide of SEQ ID NO: 1, and wherein said polynucleotide codes for a polypeptide having protein kinase D activity.

11. The process of claim 1, wherein the nucleotide sequence is a polynucleotide coding for a polypeptide comprising the amino acid sequence of SEQ ID NO: 2.

12. The process of claim 1, wherein the nucleotide sequence is a sequence which hybridizes with SEQ ID NO: 1, wherein hybridization comprises washing in 0.5×SSC at a temperature of 68° C., and which encodes a protein with protein kinase D activity.

* * * * *

SEQUENCE LISTING

```
<160> NUMBER OF SEQ ID NOS: 6

<210> SEQ ID NO 1
<211> LENGTH: 3341
<212> TYPE: DNA
<213> ORGANISM: Corynebacterium glutamicum
<220> FEATURE:
<221> NAME/KEY: CDS
<222> LOCATION: (512)..(2731)
<223> OTHER INFORMATION:

<400> SEQUENCE: 1
agaacgccat tgcttgagcg cgtcgcataa cttcacgagc caactggcca tgaagtgcat        60
cgatggggcg accaggaagg gtctcgtctt cggtaaacag gaacgcgagg atttcctcgt       120
cgctgaagcc accgtcggca agcaaggcaa taactccagg gatgaaacgg ttggtgtttt       180
ccttcttggt gctcaggaaa gcttctggaa tgtagcgaat accgtcgcgc cggaccacga       240
tcaatttgtg ttcattgacc agatccatca ccttggtgac aacaacgccg aggcgctcgg       300
ctgtctccgg aagggtcagc aatggttcat tgtcgggcag ggcgaaggaa gattcattgt       360
tggaactcac agtcttaatt tagctggttc gagctctaat ggagaatctt tagggtattt       420
ctgcgcgtgc cgggaatgaa agcaccttct tgacctttga aaacaggatg tcactaccac       480
tttttgtgta ccttccgaca tactggaacg c atg gca aac ttg aag gtc ggt        532
                                   Met Ala Asn Leu Lys Val Gly
                                     1               5 gac gtt tta gag gac agg tat cgg att gaa act ccg att gcc cgg ggt        580
Asp Val Leu Glu Asp Arg Tyr Arg Ile Glu Thr Pro Ile Ala Arg Gly
         10                  15                  20 ggt atg tct acc gtg tac agg tgc ctt gat ctt cgt tta gga cgt tcc        628
Gly Met Ser Thr Val Tyr Arg Cys Leu Asp Leu Arg Leu Gly Arg Ser
     25                  30                  35 atg gcg ctt aaa gtc atg gaa gaa gat ttc gtt gat gat ccc att ttc        676
Met Ala Leu Lys Val Met Glu Glu Asp Phe Val Asp Asp Pro Ile Phe
 40                  45                  50                  55 cgg cag cgt ttc cgt agg gaa gct cgg tca atg gcg cag cta aat cat        724
Arg Gln Arg Phe Arg Arg Glu Ala Arg Ser Met Ala Gln Leu Asn His
                 60                  65                  70 cca aat ttg gtc aat gtg tat gat ttt tcc gct act gac ggt ttg gtg        772
Pro Asn Leu Val Asn Val Tyr Asp Phe Ser Ala Thr Asp Gly Leu Val
             75                  80                  85 tat ctg gtg atg gag tta atc act ggt ggc acc ttg cgt gag ttg ctg        820
Tyr Leu Val Met Glu Leu Ile Thr Gly Gly Thr Leu Arg Glu Leu Leu
         90                  95                 100 gct gag cgg gga cct atg ccc ccg cat gct gct gtg ggc gtt atg cgt        868
Ala Glu Arg Gly Pro Met Pro Pro His Ala Ala Val Gly Val Met Arg
```

-continued

| | | | |
|---|---|---|---|
| ggg gtg ctc acg ggt ctc gcg gct gcc cac cgg gcg ggc atg gtg cac<br>Gly Val Leu Thr Gly Leu Ala Ala Ala His Arg Ala Gly Met Val His<br>120                           125                     130                         135 | 916 |

```
        105                 110                 115
ggg gtg ctc acg ggt ctc gcg gct gcc cac cgg gcg ggc atg gtg cac      916
Gly Val Leu Thr Gly Leu Ala Ala Ala His Arg Ala Gly Met Val His
120                 125                 130                 135 cgg gat atc aag cct gac aac gtg ttg atc aat agt gat cac cag gtg      964
Arg Asp Ile Lys Pro Asp Asn Val Leu Ile Asn Ser Asp His Gln Val
                140                 145                 150 aaa ctg tct gat ttc ggc ttg gtt cga gcg gct cac gcc ggc cag tct     1012
Lys Leu Ser Asp Phe Gly Leu Val Arg Ala Ala His Ala Gly Gln Ser
            155                 160                 165 cag gac aat cag att gtg ggc acg gtg gct tat ctt tcc cct gag cag     1060
Gln Asp Asn Gln Ile Val Gly Thr Val Ala Tyr Leu Ser Pro Glu Gln
        170                 175                 180 gtt gag ggc ggt gag atc ggg ccg gcc agc gac gtg tat tcg gca ggc     1108
Val Glu Gly Gly Glu Ile Gly Pro Ala Ser Asp Val Tyr Ser Ala Gly
    185                 190                 195 att gtg ctc ttt gag ctg ctc aca ggc acc acg cct ttt tcg ggc gag     1156
Ile Val Leu Phe Glu Leu Leu Thr Gly Thr Thr Pro Phe Ser Gly Glu
200                 205                 210                 215 gat gat ctc gac cat gca tac gcc cgc ctt acg gaa gtc gtg ccg gca     1204
Asp Asp Leu Asp His Ala Tyr Ala Arg Leu Thr Glu Val Val Pro Ala
                220                 225                 230 ccg agt tcg ctt atc gac ggc gtc ccc tcc ctc atc gat gag ctt gtc     1252
Pro Ser Ser Leu Ile Asp Gly Val Pro Ser Leu Ile Asp Glu Leu Val
            235                 240                 245 gcg aca gct acc tcc att aat cct gag gat cgt ttc gat gat tct gga     1300
Ala Thr Ala Thr Ser Ile Asn Pro Glu Asp Arg Phe Asp Asp Ser Gly
        250                 255                 260 gag ttt ttg tcc gca ctg gaa gat gtc gca aca gag ttg agc ttg ccg     1348
Glu Phe Leu Ser Ala Leu Glu Asp Val Ala Thr Glu Leu Ser Leu Pro
    265                 270                 275 gct ttc cgg gtc cct gtg ccg gtt aat tcc gca gcc aat agg gct aat     1396
Ala Phe Arg Val Pro Val Pro Val Asn Ser Ala Ala Asn Arg Ala Asn
280                 285                 290                 295 gcc cag gtc ccg gat gct cag cca act gat atg ttt acc acc cat atc     1444
Ala Gln Val Pro Asp Ala Gln Pro Thr Asp Met Phe Thr Thr His Ile
                300                 305                 310 ccc aag act cct gag cct gat cac act gcg atc att ccg gtg gcc tca     1492
Pro Lys Thr Pro Glu Pro Asp His Thr Ala Ile Ile Pro Val Ala Ser
            315                 320                 325 gca aat gag acg tcg att ctg cct gcg caa aac atg gca caa aat atg     1540
Ala Asn Glu Thr Ser Ile Leu Pro Ala Gln Asn Met Ala Gln Asn Met
        330                 335                 340 gcg cag aat ccg ctg caa cct ccg gaa cct gat ttc gcc ccg gag cca     1588
Ala Gln Asn Pro Leu Gln Pro Pro Glu Pro Asp Phe Ala Pro Glu Pro
    345                 350                 355 cct ccg gac aca gcg ctg aat att caa gat caa gag ctt gcg cgc gcc     1636
Pro Pro Asp Thr Ala Leu Asn Ile Gln Asp Gln Glu Leu Ala Arg Ala
360                 365                 370                 375 gat gag cca gaa att aat acc gtc agc aat cgt tcc aaa ttg aag ctg     1684
Asp Glu Pro Glu Ile Asn Thr Val Ser Asn Arg Ser Lys Leu Lys Leu
                380                 385                 390 acg ttg tgg tca att ttc gtg gtc gca gtg atc gct gct gtt gct gtt     1732
Thr Leu Trp Ser Ile Phe Val Val Ala Val Ile Ala Ala Val Ala Val
            395                 400                 405 ggc ggt tgg tgg ttc ggt tca ggc cgt tac ggt gag att ccg cag gtg     1780
Gly Gly Trp Trp Phe Gly Ser Gly Arg Tyr Gly Glu Ile Pro Gln Val
        410                 415                 420 ttg ggc atg gat gag gtc cag gca gta gct gtt gta gag gaa gct ggt     1828
```

```
                  Leu Gly Met Asp Glu Val Gln Ala Val Ala Val Val Glu Glu Ala Gly
                      425                 430                 435 ttc gtg gca gtg gct gaa cct cag tat gac aat gag gtt ccc act ggt      1876
Phe Val Ala Val Ala Glu Pro Gln Tyr Asp Asn Glu Val Pro Thr Gly
440                 445                 450                 455 tcg att att ggg act gaa cct tct ttt ggt gag cgc ctt cct cgc ggc      1924
Ser Ile Ile Gly Thr Glu Pro Ser Phe Gly Glu Arg Leu Pro Arg Gly
                    460                 465                 470 gag gat gtt tct gtc ctc gtc tct caa ggg cgt ccc gtg gtg ccg gat      1972
Glu Asp Val Ser Val Leu Val Ser Gln Gly Arg Pro Val Val Pro Asp
                475                 480                 485 ctt agc gag gat cga tcc tta agc acc gtt cgt gaa gag ttg gaa cag      2020
Leu Ser Glu Asp Arg Ser Leu Ser Thr Val Arg Glu Glu Leu Glu Gln
            490                 495                 500 cgc acg ttc gtc tgg gtt gat ggc cca ggt gaa tat tct gac gat gtt      2068
Arg Thr Phe Val Trp Val Asp Gly Pro Gly Glu Tyr Ser Asp Asp Val
        505                 510                 515 cca gaa gga caa gta gtt tct ttt aca ccg tcg tca ggc acg cag ctt      2116
Pro Glu Gly Gln Val Val Ser Phe Thr Pro Ser Ser Gly Thr Gln Leu
520                 525                 530                 535 gat gtt ggt gaa acc gtg cag atc cat ttg agc cga ggc ccc gcc ccg      2164
Asp Val Gly Glu Thr Val Gln Ile His Leu Ser Arg Gly Pro Ala Pro
                    540                 545                 550 gtt gag att cct gat gtc tct ggc atg gga gtg gat cag gca aca cgt      2212
Val Glu Ile Pro Asp Val Ser Gly Met Gly Val Asp Gln Ala Thr Arg
                555                 560                 565 gtg ttg gag cgc gca ggt ttg agc gtc gag cgt act gaa gaa ggc ttt      2260
Val Leu Glu Arg Ala Gly Leu Ser Val Glu Arg Thr Glu Glu Gly Phe
            570                 575                 580 gat gct gag aca cca aat ggt gat gtc tac ggg act tcg ccc aag gta      2308
Asp Ala Glu Thr Pro Asn Gly Asp Val Tyr Gly Thr Ser Pro Lys Val
        585                 590                 595 tct act gag gtc aag cgc gga acc tct gtt gtg ctg cag gtg tcc aat      2356
Ser Thr Glu Val Lys Arg Gly Thr Ser Val Val Leu Gln Val Ser Asn
600                 605                 610                 615 gct att tcg gta ccg gat gtg gtg ggt atg acc aag gac gaa gcc acc      2404
Ala Ile Ser Val Pro Asp Val Val Gly Met Thr Lys Asp Glu Ala Thr
                    620                 625                 630 gcg gcg ctt gcg gaa gaa gga ttg gtc gtg gcg tcg aca agc att att      2452
Ala Ala Leu Ala Glu Glu Gly Leu Val Val Ala Ser Thr Ser Ile Ile
                635                 640                 645 cct ggt gag gcg gcg agc tcc gct gac gcc gtc gtg acc gtc gag cct      2500
Pro Gly Glu Ala Ala Ser Ser Ala Asp Ala Val Val Thr Val Glu Pro
            650                 655                 660 gaa tcc ggc agc cgc gtt gat cca gcg cat ccg cag gtc agc ctc ggg      2548
Glu Ser Gly Ser Arg Val Asp Pro Ala His Pro Gln Val Ser Leu Gly
        665                 670                 675 tta gct ggg gag att caa gtt cca agc gtg gtt gga cgt aag gtt agc      2596
Leu Ala Gly Glu Ile Gln Val Pro Ser Val Val Gly Arg Lys Val Ser
680                 685                 690                 695 gat gct cga agc att ctg gaa gaa gcc ggt tta acg ctg aca act gat      2644
Asp Ala Arg Ser Ile Leu Glu Glu Ala Gly Leu Thr Leu Thr Thr Asp
                    700                 705                 710 gcg gac gac aac gat cga att tat agt caa acc cct cgt gca cgc agc      2692
Ala Asp Asp Asn Asp Arg Ile Tyr Ser Gln Thr Pro Arg Ala Arg Ser
                715                 720                 725 gaa gtc tcg gta ggg gga gaa gtt aca gta agg gcg ttt tagtggttcc      2741
Glu Val Ser Val Gly Gly Glu Val Thr Val Arg Ala Phe
            730                 735                 740
```

-continued

```
ctcgttgcag caatggcgaa aacctgctct catcctggcc attttgacgg tgctaggcgt    2801
actcctgacc cattggttcg cctggccact cacctggccg ctggggctgc gtcttcccgt    2861
tgatgtagag gtgtactggc agggtgcgcg cgagttttgg ctcgccgatg atctctacga    2921
catcaggtat gacaccactt tcgacaactt gccgttcacc tatccccctt tcggtgcgtt    2981
ggtgttcacc ccattgtggt ggattcatga cctctttggt cttctcgtca ccgaacgtgt    3041
cttcgcgcta atcacgctgc tcaccaccta cgctgtggca gttttcctgc tccgcctggc    3101
cggcgtgcgc gatcgtgtgt gggaattcgt cgcattcgca gccctgctcg tgtccgcgcc    3161
ggtgtatttc acactcaata ttgggcaaat aaacgtcatg ctcatggctt taacgctttt    3221
cgacgtcgcc ctccccccgca gcacgcgcca ttcaggcgtg ctcaaatacg tgccactcgg    3281
cgtactcacc ggcattgccg ctgcgatcaa actaaccccca ctagtgttcg ggctgtattt    3341
```

<210> SEQ ID NO 2
<211> LENGTH: 740
<212> TYPE: PRT
<213> ORGANISM: Corynebacterium glutamicum

<400> SEQUENCE: 2

```
Met Ala Asn Leu Lys Val Gly Asp Val Leu Glu Asp Arg Tyr Arg Ile
1               5                   10                  15

Glu Thr Pro Ile Ala Arg Gly Gly Met Ser Thr Val Tyr Arg Cys Leu
            20                  25                  30

Asp Leu Arg Leu Gly Arg Ser Met Ala Leu Lys Val Met Glu Glu Asp
        35                  40                  45

Phe Val Asp Asp Pro Ile Phe Arg Gln Arg Phe Arg Arg Glu Ala Arg
    50                  55                  60

Ser Met Ala Gln Leu Asn His Pro Asn Leu Val Asn Val Tyr Asp Phe
65                  70                  75                  80

Ser Ala Thr Asp Gly Leu Val Tyr Leu Val Met Glu Leu Ile Thr Gly
                85                  90                  95

Gly Thr Leu Arg Glu Leu Leu Ala Glu Arg Gly Pro Met Pro Pro His
            100                 105                 110

Ala Ala Val Gly Val Met Arg Gly Val Leu Thr Gly Leu Ala Ala Ala
        115                 120                 125

His Arg Ala Gly Met Val His Arg Asp Ile Lys Pro Asp Asn Val Leu
    130                 135                 140

Ile Asn Ser Asp His Gln Val Lys Leu Ser Asp Phe Gly Leu Val Arg
145                 150                 155                 160

Ala Ala His Ala Gly Gln Ser Gln Asp Asn Gln Ile Val Gly Thr Val
                165                 170                 175

Ala Tyr Leu Ser Pro Glu Gln Val Glu Gly Gly Glu Ile Gly Pro Ala
            180                 185                 190

Ser Asp Val Tyr Ser Ala Gly Ile Val Leu Phe Glu Leu Leu Thr Gly
        195                 200                 205

Thr Thr Pro Phe Ser Gly Glu Asp Leu Asp His Ala Tyr Ala Arg
    210                 215                 220

Leu Thr Glu Val Val Pro Ala Pro Ser Ser Leu Ile Asp Gly Val Pro
225                 230                 235                 240

Ser Leu Ile Asp Glu Leu Val Ala Thr Ala Thr Ser Ile Asn Pro Glu
                245                 250                 255

Asp Arg Phe Asp Asp Ser Gly Glu Phe Leu Ser Ala Leu Glu Asp Val
            260                 265                 270
```

-continued

```
Ala Thr Glu Leu Ser Leu Pro Ala Phe Arg Val Pro Val Asn
        275                 280                 285

Ser Ala Ala Asn Arg Ala Asn Ala Gln Val Pro Asp Ala Gln Pro Thr
290                 295                 300

Asp Met Phe Thr Thr His Ile Pro Lys Thr Pro Glu Pro Asp His Thr
305                 310                 315                 320

Ala Ile Ile Pro Val Ala Ser Ala Asn Glu Thr Ser Ile Leu Pro Ala
                325                 330                 335

Gln Asn Met Ala Gln Asn Met Ala Gln Asn Pro Leu Gln Pro Pro Glu
                340                 345                 350

Pro Asp Phe Ala Pro Glu Pro Pro Asp Thr Ala Leu Asn Ile Gln
            355                 360                 365

Asp Gln Glu Leu Ala Arg Ala Asp Glu Pro Gly Ile Asn Thr Val Ser
        370                 375                 380

Asn Arg Ser Lys Leu Lys Leu Thr Leu Trp Ser Ile Phe Val Ala
385                 390                 395                 400

Val Ile Ala Ala Val Ala Val Gly Gly Trp Trp Phe Gly Ser Gly Arg
                405                 410                 415

Tyr Gly Glu Ile Pro Gln Val Leu Gly Met Asp Glu Val Gln Ala Val
            420                 425                 430

Ala Val Val Glu Glu Ala Gly Phe Val Ala Val Ala Glu Pro Gln Tyr
            435                 440                 445

Asp Asn Glu Val Pro Thr Gly Ser Ile Ile Gly Thr Glu Pro Ser Phe
450                 455                 460

Gly Glu Arg Leu Pro Arg Gly Glu Asp Val Ser Val Leu Val Ser Gln
465                 470                 475                 480

Gly Arg Pro Val Val Pro Asp Leu Ser Glu Asp Arg Ser Leu Ser Thr
                485                 490                 495

Val Arg Glu Glu Leu Glu Gln Arg Thr Phe Val Trp Val Asp Gly Pro
            500                 505                 510

Gly Glu Tyr Ser Asp Asp Val Pro Glu Gly Gln Val Val Ser Phe Thr
        515                 520                 525

Pro Ser Ser Gly Thr Gln Leu Asp Val Gly Glu Thr Val Gln Ile His
    530                 535                 540

Leu Ser Arg Gly Pro Ala Pro Val Glu Ile Pro Asp Val Ser Gly Met
545                 550                 555                 560

Gly Val Asp Gln Ala Thr Arg Val Leu Glu Arg Ala Gly Leu Ser Val
                565                 570                 575

Glu Arg Thr Glu Glu Gly Phe Asp Ala Glu Thr Pro Asn Gly Asp Val
            580                 585                 590

Tyr Gly Thr Ser Pro Lys Val Ser Thr Glu Val Lys Arg Gly Thr Ser
        595                 600                 605

Val Val Leu Gln Val Ser Asn Ala Ile Ser Val Pro Asp Val Val Gly
    610                 615                 620

Met Thr Lys Asp Glu Ala Thr Ala Ala Leu Ala Glu Glu Gly Leu Val
625                 630                 635                 640

Val Ala Ser Thr Ser Ile Ile Pro Gly Glu Ala Ala Ser Ser Ala Asp
                645                 650                 655

Ala Val Val Thr Val Glu Pro Glu Ser Gly Ser Arg Val Asp Pro Ala
            660                 665                 670

His Pro Gln Val Ser Leu Gly Leu Ala Gly Glu Ile Gln Val Pro Ser
        675                 680                 685

Val Val Gly Arg Lys Val Ser Asp Ala Arg Ser Ile Leu Glu Glu Ala
```

-continued 690             695             700
Gly Leu Thr Leu Thr Thr Asp Ala Asp Asp Asn Asp Arg Ile Tyr Ser
705                 710                 715                 720

Gln Thr Pro Arg Ala Arg Ser Glu Val Ser Val Gly Gly Val Thr
                725                 730                 735

Val Arg Ala Phe
            740

<210> SEQ ID NO 3
<211> LENGTH: 3341
<212> TYPE: DNA
<213> ORGANISM: Corynebacterium glutamicum
<220> FEATURE:
<221> NAME/KEY: CDS
<222> LOCATION: (512)..(2731)
<223> OTHER INFORMATION:
<220> FEATURE:
<221> NAME/KEY: misc_feature
<222> LOCATION: (2501)..(2501)
<223> OTHER INFORMATION: G-A transition
<220> FEATURE:
<221> NAME/KEY: misc_feature
<222> LOCATION: (2507)..(2507)
<223> OTHER INFORMATION: G-A transition

<400> SEQUENCE: 3
agaacgccat tgcttgagcg cgtcgcataa cttcacgagc caactggcca tgaagtgcat      60
cgatggggcg accaggaagg gtctcgtctt cggtaaacag gaacgcgagg atttcctcgt     120
cgctgaagcc accgtcggca agcaaggcaa taactccagg gatgaaacgg ttggtgtttt     180
ccttcttggt gctcaggaaa gcttctggaa tgtagcgaat accgtcgcgc cggaccacga     240
tcaatttgtg ttcattgacc agatccatca ccttggtgac aacaacgccg aggcgctcgg     300
ctgtctccgg aagggtcagc aatggttcat tgtcgggcag ggcgaaggaa gattcattgt     360
tggaactcac agtcttaatt tagctggttc gagctctaat ggagaatctt tagggtattt     420
ctgcgcgtgc cgggaatgaa agcaccttct tgacctttga aaacaggatg tcactaccac     480
tttttgtgta ccttccgaca tactggaacg c atg gca aac ttg aag gtc ggt        532
                                    Met Ala Asn Leu Lys Val Gly
                                     1               5 gac gtt tta gag gac agg tat cgg att gaa act ccg att gcc cgg ggt      580
Asp Val Leu Glu Asp Arg Tyr Arg Ile Glu Thr Pro Ile Ala Arg Gly
         10                  15                  20 ggt atg tct acc gtg tac agg tgc ctt gat ctt cgt tta gga cgt tcc      628
Gly Met Ser Thr Val Tyr Arg Cys Leu Asp Leu Arg Leu Gly Arg Ser
     25                  30                  35 atg gcg ctt aaa gtc atg gaa gaa gat ttc gtt gat gat ccc att ttc      676
Met Ala Leu Lys Val Met Glu Glu Asp Phe Val Asp Asp Pro Ile Phe
 40                  45                  50                  55 cgg cag cgt ttc cgt agg gaa gct cgg tca atg gcg cag cta aat cat      724
Arg Gln Arg Phe Arg Arg Glu Ala Arg Ser Met Ala Gln Leu Asn His
                 60                  65                  70 cca aat ttg gtc aat gtg tat gat ttt tcc gct act gac ggt ttg gtg      772
Pro Asn Leu Val Asn Val Tyr Asp Phe Ser Ala Thr Asp Gly Leu Val
             75                  80                  85 tat ctg gtg atg gag tta atc act ggt ggc acc ttg cgt gag ttg ctg      820
Tyr Leu Val Met Glu Leu Ile Thr Gly Gly Thr Leu Arg Glu Leu Leu
         90                  95                 100 gct gag cgg gga cct atg ccc ccg cat gct gct gtg ggc gtt atg cgt      868
Ala Glu Arg Gly Pro Met Pro Pro His Ala Ala Val Gly Val Met Arg
    105                 110                 115

```
                                                                    -continued ggg gtg ctc acg ggt ctc gcg gct gcc cac cgg gcg ggc atg gtg cac        916
Gly Val Leu Thr Gly Leu Ala Ala Ala His Arg Ala Gly Met Val His
120             125                 130                 135 cgg gat atc aag cct gac aac gtg ttg atc aat agt gat cac cag gtg        964
Arg Asp Ile Lys Pro Asp Asn Val Leu Ile Asn Ser Asp His Gln Val
                140                 145                 150 aaa ctg tct gat ttc ggc ttg gtt cga gcg gct cac gcc ggc cag tct       1012
Lys Leu Ser Asp Phe Gly Leu Val Arg Ala Ala His Ala Gly Gln Ser
            155                 160                 165 cag gac aat cag att gtg ggc acg gtg gct tat ctt tcc cct gag cag       1060
Gln Asp Asn Gln Ile Val Gly Thr Val Ala Tyr Leu Ser Pro Glu Gln
        170                 175                 180 gtt gag ggc ggt gag atc ggg ccg gcc agc gac gtg tat tcg gca ggc       1108
Val Glu Gly Gly Glu Ile Gly Pro Ala Ser Asp Val Tyr Ser Ala Gly
    185                 190                 195 att gtg ctc ttt gag ctg ctc aca ggc acc acg cct ttt tcg ggc gag       1156
Ile Val Leu Phe Glu Leu Leu Thr Gly Thr Thr Pro Phe Ser Gly Glu
200                 205                 210                 215 gat gat ctc gac cat gca tac gcc cgc ctt acg gaa gtc gtg ccg gca       1204
Asp Asp Leu Asp His Ala Tyr Ala Arg Leu Thr Glu Val Val Pro Ala
                220                 225                 230 ccg agt tcg ctt atc gac ggc gtc ccc tcc ctc atc gat gag ctt gtc       1252
Pro Ser Ser Leu Ile Asp Gly Val Pro Ser Leu Ile Asp Glu Leu Val
            235                 240                 245 gcg aca gct acc tcc att aat cct gag gat cgt ttc gat gat tct gga       1300
Ala Thr Ala Thr Ser Ile Asn Pro Glu Asp Arg Phe Asp Asp Ser Gly
        250                 255                 260 gag ttt ttg tcc gca ctg gaa gat gtc gca aca gag ttg agc ttg ccg       1348
Glu Phe Leu Ser Ala Leu Glu Asp Val Ala Thr Glu Leu Ser Leu Pro
    265                 270                 275 gct ttc cgg gtc cct gtg ccg gtt aat tcc gca gcc aat agg gct aat       1396
Ala Phe Arg Val Pro Val Pro Val Asn Ser Ala Ala Asn Arg Ala Asn
280                 285                 290                 295 gcc cag gtc ccg gat gct cag cca act gat atg ttt acc acc cat atc       1444
Ala Gln Val Pro Asp Ala Gln Pro Thr Asp Met Phe Thr Thr His Ile
                300                 305                 310 ccc aag act cct gag cct gat cac act gcg atc att ccg gtg gcc tca       1492
Pro Lys Thr Pro Glu Pro Asp His Thr Ala Ile Ile Pro Val Ala Ser
            315                 320                 325 gca aat gag acg tcg att ctg cct gcg caa aac atg gca caa aat atg       1540
Ala Asn Glu Thr Ser Ile Leu Pro Ala Gln Asn Met Ala Gln Asn Met
        330                 335                 340 gcg cag aat ccg ctg caa cct ccg gaa cct gat ttc gcc ccg gag cca       1588
Ala Gln Asn Pro Leu Gln Pro Pro Glu Pro Asp Phe Ala Pro Glu Pro
    345                 350                 355 cct ccg gac aca gcg ctg aat att caa gat caa gag ctt gcg cgc gcc       1636
Pro Pro Asp Thr Ala Leu Asn Ile Gln Asp Gln Glu Leu Ala Arg Ala
360                 365                 370                 375 gat gag cca gaa att aat acc gtc agc aat cgt tcc aaa ttg aag ctg       1684
Asp Glu Pro Glu Ile Asn Thr Val Ser Asn Arg Ser Lys Leu Lys Leu
                380                 385                 390 acg ttg tgg tca att ttc gtg gtc gca gtg atc gct gct gtt gct gtt       1732
Thr Leu Trp Ser Ile Phe Val Val Ala Val Ile Ala Ala Val Ala Val
            395                 400                 405 ggc ggt tgg tgg ttc ggt tca ggc cgt tac ggt gag att ccg cag gtg       1780
Gly Gly Trp Trp Phe Gly Ser Gly Arg Tyr Gly Glu Ile Pro Gln Val
        410                 415                 420 ttg ggc atg gat gag gtc cag gca gta gct gtt gta gag gaa gct ggt       1828
Leu Gly Met Asp Glu Val Gln Ala Val Ala Val Val Glu Glu Ala Gly
    425                 430                 435
```

-continued

| | | |
|---|---|---|
| ttc gtg gca gtg gct gaa cct cag tat gac aat gag gtt ccc act ggt<br>Phe Val Ala Val Ala Glu Pro Gln Tyr Asp Asn Glu Val Pro Thr Gly<br>440                    445                    450                    455 | | 1876 |
| tcg att att ggg act gaa cct tct ttt ggt gag cgc ctt cct cgc ggc<br>Ser Ile Ile Gly Thr Glu Pro Ser Phe Gly Glu Arg Leu Pro Arg Gly<br>                   460                    465                    470 | | 1924 |
| gag gat gtt tct gtc ctc gtc tct caa ggg cgt ccc gtg gtg ccg gat<br>Glu Asp Val Ser Val Leu Val Ser Gln Gly Arg Pro Val Val Pro Asp<br>            475                    480                    485 | | 1972 |
| ctt agc gag gat cga tcc tta agc acc gtt cgt gaa gag ttg gaa cag<br>Leu Ser Glu Asp Arg Ser Leu Ser Thr Val Arg Glu Glu Leu Glu Gln<br>                   490                    495                    500 | | 2020 |
| cgc acg ttc gtc tgg gtt gat ggc cca ggt gaa tat tct gac gat gtt<br>Arg Thr Phe Val Trp Val Asp Gly Pro Gly Glu Tyr Ser Asp Asp Val<br>505                    510                    515 | | 2068 |
| cca gaa gga caa gta gtt tct ttt aca ccg tcg tca ggc acg cag ctt<br>Pro Glu Gly Gln Val Val Ser Phe Thr Pro Ser Ser Gly Thr Gln Leu<br>520                    525                    530                    535 | | 2116 |
| gat gtt ggt gaa acc gtg cag atc cat ttg agc cga ggc ccc gcc ccg<br>Asp Val Gly Glu Thr Val Gln Ile His Leu Ser Arg Gly Pro Ala Pro<br>                   540                    545                    550 | | 2164 |
| gtt gag att cct gat gtc tct ggc atg gga gtg gat cag gca aca cgt<br>Val Glu Ile Pro Asp Val Ser Gly Met Gly Val Asp Gln Ala Thr Arg<br>            555                    560                    565 | | 2212 |
| gtg ttg gag cgc gca ggt ttg agc gtc gag cgt act gaa gaa ggc ttt<br>Val Leu Glu Arg Ala Gly Leu Ser Val Glu Arg Thr Glu Glu Gly Phe<br>                   570                    575                    580 | | 2260 |
| gat gct gag aca cca aat ggt gat gtc tac ggg act tcg ccc aag gta<br>Asp Ala Glu Thr Pro Asn Gly Asp Val Tyr Gly Thr Ser Pro Lys Val<br>585                    590                    595 | | 2308 |
| tct act gag gtc aag cgc gga acc tct gtt gtg ctg cag gtg tcc aat<br>Ser Thr Glu Val Lys Arg Gly Thr Ser Val Val Leu Gln Val Ser Asn<br>600                    605                    610                    615 | | 2356 |
| gct att tcg gta ccg gat gtg gtg ggt atg acc aag gac gaa gcc acc<br>Ala Ile Ser Val Pro Asp Val Val Gly Met Thr Lys Asp Glu Ala Thr<br>                   620                    625                    630 | | 2404 |
| gcg gcg ctt gcg gaa gaa gga ttg gtc gtg gcg tcg aca agc att att<br>Ala Ala Leu Ala Glu Glu Gly Leu Val Val Ala Ser Thr Ser Ile Ile<br>            635                    640                    645 | | 2452 |
| cct ggt gag gcg gcg agc tcc gct gac gcc gtc gtg acc gtc gag cct<br>Pro Gly Glu Ala Ala Ser Ser Ala Asp Ala Val Val Thr Val Glu Pro<br>                 650                    655                    660 | | 2500 |
| aaa tcc agc agc cgc gtt gat cca gcg cat ccg cag gtc agc ctc ggg<br>Lys Ser Ser Ser Arg Val Asp Pro Ala His Pro Gln Val Ser Leu Gly<br>665                    670                    675 | | 2548 |
| tta gct ggg gag att caa gtt cca agc gtg gtt gga cgt aag gtt agc<br>Leu Ala Gly Glu Ile Gln Val Pro Ser Val Val Gly Arg Lys Val Ser<br>680                    685                    690                    695 | | 2596 |
| gat gct cga agc att ctg gaa gaa gcc ggt tta acg ctg aca act gat<br>Asp Ala Arg Ser Ile Leu Glu Glu Ala Gly Leu Thr Leu Thr Thr Asp<br>                 700                    705                    710 | | 2644 |
| gcg gac gac aac gat cga att tat agt caa acc cct cgt gca cgc agc<br>Ala Asp Asp Asn Asp Arg Ile Tyr Ser Gln Thr Pro Arg Ala Arg Ser<br>            715                    720                    725 | | 2692 |
| gaa gtc tcg gta ggg gga gaa gtt aca gta agg gcg ttt tagtggttcc<br>Glu Val Ser Val Gly Gly Glu Val Thr Val Arg Ala Phe<br>                 730                    735                    740 | | 2741 |
| ctcgttgcag caatggcgaa aacctgctct catcctggcc attttgacgg tgctaggcgt | | 2801 |

-continued

```
actcctgacc cattggttcg cctggccact cacctggccg ctggggctgc gtcttcccgt    2861
tgatgtagag gtgtactggc agggtgcgcg cgagttttgg ctcgccgatg atctctacga    2921
catcaggtat gacaccactt tcgacaactt gccgttcacc tatccccctt tcggtgcgtt    2981
ggtgttcacc ccattgtggt ggattcatga cctctttggt cttctcgtca ccgaacgtgt    3041
cttcgcgcta atcacgctgc tcaccaccta cgctgtggca gttttcctgc tccgcctggc    3101
cggcgtgcgc gatcgtgtgt gggaattcgt cgcattcgca gccctgctcg tgtccgcgcc    3161
ggtgtatttc acactcaata ttgggcaaat aaacgtcatg ctcatggctt aacgctttt    3221 cgacgtcgcc ctcccccgca gcacgcgcca ttcaggcgtg ctcaaatacg tgccactcgg    3281
cgtactcacc ggcattgccg ctgcgatcaa actaacccca ctagtgttcg ggctgtattt    3341
```

<210> SEQ ID NO 4
<211> LENGTH: 740
<212> TYPE: PRT
<213> ORGANISM: Corynebacterium glutamicum
<220> FEATURE:
<221> NAME/KEY: misc_feature
<222> LOCATION: (2501)..(2501)
<223> OTHER INFORMATION: G-A transition
<220> FEATURE:
<221> NAME/KEY: misc_feature
<222> LOCATION: (2507)..(2507)
<223> OTHER INFORMATION: G-A transition

<400> SEQUENCE: 4

```
Met Ala Asn Leu Lys Val Gly Asp Val Leu Glu Asp Arg Tyr Arg Ile
1               5                   10                  15

Glu Thr Pro Ile Ala Arg Gly Gly Met Ser Thr Val Tyr Arg Cys Leu
            20                  25                  30

Asp Leu Arg Leu Gly Arg Ser Met Ala Leu Lys Val Met Glu Glu Asp
        35                  40                  45

Phe Val Asp Asp Pro Ile Phe Arg Gln Arg Phe Arg Arg Glu Ala Arg
    50                  55                  60

Ser Met Ala Gln Leu Asn His Pro Asn Leu Val Asn Val Tyr Asp Phe
65                  70                  75                  80

Ser Ala Thr Asp Gly Leu Val Tyr Leu Val Met Glu Leu Ile Thr Gly
                85                  90                  95

Gly Thr Leu Arg Glu Leu Leu Ala Glu Arg Gly Pro Met Pro Pro His
            100                 105                 110

Ala Ala Val Gly Val Met Arg Gly Val Leu Thr Gly Leu Ala Ala Ala
        115                 120                 125

His Arg Ala Gly Met Val His Arg Asp Ile Lys Pro Asp Asn Val Leu
    130                 135                 140

Ile Asn Ser Asp His Gln Val Lys Leu Ser Asp Phe Gly Leu Val Arg
145                 150                 155                 160

Ala Ala His Ala Gly Gln Ser Gln Asp Asn Gln Ile Val Gly Thr Val
                165                 170                 175

Ala Tyr Leu Ser Pro Glu Gln Val Glu Gly Glu Ile Gly Pro Ala
            180                 185                 190

Ser Asp Val Tyr Ser Ala Gly Ile Val Leu Phe Glu Leu Leu Thr Gly
        195                 200                 205

Thr Thr Pro Phe Ser Gly Glu Asp Asp Leu Asp His Ala Tyr Ala Arg
    210                 215                 220

Leu Thr Glu Val Val Pro Ala Pro Ser Ser Leu Ile Asp Gly Val Pro
225                 230                 235                 240
```

```
Ser Leu Ile Asp Glu Leu Val Ala Thr Ala Thr Ser Ile Asn Pro Glu
                245                 250                 255

Asp Arg Phe Asp Asp Ser Gly Glu Phe Leu Ser Ala Leu Glu Asp Val
            260                 265                 270

Ala Thr Glu Leu Ser Leu Pro Ala Phe Arg Val Pro Val Pro Val Asn
        275                 280                 285

Ser Ala Ala Asn Arg Ala Asn Ala Gln Val Pro Asp Ala Gln Pro Thr
    290                 295                 300

Asp Met Phe Thr Thr His Ile Pro Lys Thr Pro Glu Pro Asp His Thr
305                 310                 315                 320

Ala Ile Ile Pro Val Ala Ser Ala Asn Glu Thr Ser Ile Leu Pro Ala
                325                 330                 335

Gln Asn Met Ala Gln Asn Met Ala Gln Asn Pro Leu Gln Pro Pro Glu
            340                 345                 350

Pro Asp Phe Ala Pro Glu Pro Pro Asp Thr Ala Leu Asn Ile Gln
        355                 360                 365

Asp Gln Glu Leu Ala Arg Ala Asp Glu Pro Glu Ile Asn Thr Val Ser
    370                 375                 380

Asn Arg Ser Lys Leu Lys Leu Thr Leu Trp Ser Ile Phe Val Val Ala
385                 390                 395                 400

Val Ile Ala Ala Val Ala Val Gly Gly Trp Trp Phe Gly Ser Gly Arg
                405                 410                 415

Tyr Gly Glu Ile Pro Gln Val Leu Gly Met Asp Glu Val Gln Ala Val
            420                 425                 430

Ala Val Val Glu Glu Ala Gly Phe Val Ala Val Ala Glu Pro Gln Tyr
        435                 440                 445

Asp Asn Glu Val Pro Thr Gly Ser Ile Ile Gly Thr Glu Pro Ser Phe
    450                 455                 460

Gly Glu Arg Leu Pro Arg Gly Glu Asp Val Ser Val Leu Val Ser Gln
465                 470                 475                 480

Gly Arg Pro Val Val Pro Asp Leu Ser Glu Asp Arg Ser Leu Ser Thr
                485                 490                 495

Val Arg Glu Glu Leu Glu Gln Arg Thr Phe Val Trp Val Asp Gly Pro
            500                 505                 510

Gly Glu Tyr Ser Asp Asp Val Pro Glu Gly Gln Val Val Ser Phe Thr
        515                 520                 525

Pro Ser Ser Gly Thr Gln Leu Asp Val Gly Glu Thr Val Gln Ile His
    530                 535                 540

Leu Ser Arg Gly Pro Ala Pro Val Glu Ile Pro Asp Val Ser Gly Met
545                 550                 555                 560

Gly Val Asp Gln Ala Thr Arg Val Leu Glu Arg Ala Gly Leu Ser Val
                565                 570                 575

Glu Arg Thr Glu Glu Gly Phe Asp Ala Glu Thr Pro Asn Gly Asp Val
            580                 585                 590

Tyr Gly Thr Ser Pro Lys Val Ser Thr Glu Val Lys Arg Gly Thr Ser
        595                 600                 605

Val Val Leu Gln Val Ser Asn Ala Ile Ser Val Pro Asp Val Val Gly
    610                 615                 620

Met Thr Lys Asp Glu Ala Thr Ala Leu Ala Glu Glu Gly Leu Val
625                 630                 635                 640

Val Ala Ser Thr Ser Ile Ile Pro Gly Glu Ala Ala Ser Ser Ala Asp
                645                 650                 655

Ala Val Val Thr Val Glu Pro Lys Ser Ser Ser Arg Val Asp Pro Ala
```

```
                          660                665                670
           His Pro Gln Val Ser Leu Gly Leu Ala Gly Glu Ile Gln Val Pro Ser
                   675                680                685
           Val Val Gly Arg Lys Val Ser Asp Ala Arg Ser Ile Leu Glu Glu Ala
                   690                695                700
           Gly Leu Thr Leu Thr Thr Asp Ala Asp Asp Asn Asp Arg Ile Tyr Ser
           705                710                715                720
           Gln Thr Pro Arg Ala Arg Ser Glu Val Ser Val Gly Gly Glu Val Thr
                           725                730                735
           Val Arg Ala Phe
                   740

<210> SEQ ID NO 5
<211> LENGTH: 26
<212> TYPE: DNA
<213> ORGANISM: Artificial Sequence
<220> FEATURE:
<223> OTHER INFORMATION: Synthetic DNA

<400> SEQUENCE: 5
tctagacggt tggtggttcg gttcag                                         26

<210> SEQ ID NO 6
<211> LENGTH: 26
<212> TYPE: DNA
<213> ORGANISM: Artificial Sequence
<220> FEATURE:
<223> OTHER INFORMATION: Synthetic DNA

<400> SEQUENCE: 6
tctagacgcg gcaatgccgg tgagta                                         26
```